United States Patent [19]

Kasuga et al.

[11] Patent Number: 5,238,946
[45] Date of Patent: Aug. 24, 1993

[54] THERAPEUTIC AGENT FOR GASTRITIS

[75] Inventors: Kazunori Kasuga; Haruo Sekiguchi, both of Saitama; Katsuhiro Hamada, Tochigi; Jun Imai, Kanagawa; Shinji Kamijo, Tokyo, all of Japan

[73] Assignee: Kyorin Seiyaku Kabushiki Kaisha, Tokyo, Japan

[21] Appl. No.: 397,371

[22] Filed: Aug. 21, 1989

Related U.S. Application Data

[63] Continuation of Ser. No. 65,785, Jun. 24, 1987, abandoned.

[30] Foreign Application Priority Data

Jun. 26, 1986 [JP] Japan ................. 61-150592

[51] Int. Cl.$^5$ ........................... A61K 31/445
[52] U.S. Cl. ........................................ 514/327
[58] Field of Search ................. 514/312, 327

[56] References Cited

PUBLICATIONS

*Chemical Abstracts*, vol. 92 (1980) 174158x.
*The Merck Manual* (1987) pp. 734–739.

Primary Examiner—Zohreh A. Fay
Attorney, Agent, or Firm—McAulay Fisher Nissen Goldgerg & Kiel

[57] ABSTRACT

A therapeutic pharmaceutical composition containing 3,4,5-trimethoxy-N-3-piperidylbenzamide (troxipide) as an active ingredient for gastritis in admixture with an inert pharmaceutical carrier. The composition may be administered orally in the forms of tablets, capsules, granules and fine granules.

3 Claims, No Drawings

THERAPEUTIC AGENT FOR GASTRITIS

This is a continuation of application Ser. No. 07/065,785, filed Jun. 24, 1987 now abandoned.

BACKGROUND OF THE INVENTION

Gastritis is pathologically an inflammatory process of stomach, particularly of the gastric mucosa. It has been known that an acute gastritis is often induced by ingestion by anti-inflammatory agents (aspirin, etc.) or alcohol (ethanol), by the emotional stress or by the flowback of bile into the stomach. Furthermore, it may occasionally result from a mistaken ingestion of corrosive acid or alkali.

3,4,5-trimethoxy-N-3-piperidylbenzamide (international nonproprietary name (INN): troxipide) having a chemical structure shown below has been invented by T. Irikura, K. Kasuga and M. Segawa as an anti-ulcer compound (Japanese Patent Publication No. Sho 50-28436). There are many reports on the anti-ulcer effects of troxipide both experimentally and clinically. While, therapeutic effects of troxipide on gastritis have never been publicly known.

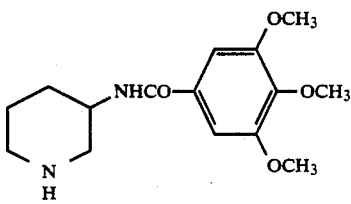

SUMMARY OF THE INVENTION

The object of the present invention relates to a novel therapeutic agent containing troxipide which is effective for gastritis.

DETAILED DESCRIPTION OF THE INVENTION

The present invention has been achieved by our discovery of prominent effects of troxipide on acute gastric lesions which are known as experimental models of the gastritis. Namely, the present inventors have searched for an effective compound which protects gastric lesions induced by aspirin, 0.6N HCl, water-immersion stress and ethanol, respectively, in rats, and it has been revealed that troxipide is highly effective though it differs entirely in chemical structure from the known effective compounds for gastritis.

As compared with cetraxate hydrochloride, an active ingredient of clinically available agent for gastritis, troxipide such much more potent protecting effects against gastric lesions induced by aspirin, 0.6N HCl and water-immersion stress. Troxipide has almost equal potency to that of cetraxate hydrochloride against ethanol-induced gastric lesions. While it is known that troxipide can be used as an effective and safe therapeutic agent for the treatment of ulcers in man, we have now discovered that troxipide is effective for the treatment of gastritis in man.

The pharmaceutical composition of the present invention may be administered orally, for example, tablets, capsules, granules, and fine granules. These formulations can be prepared by usual pharmaceutical techniques using a vehicle such as starch or low-substituted hydroxypropylcellulose as an excipient, hydroxypropylcellulose or carboxymethylcellulose as a binder, magnesium stearate or starch as a lubricant and color, taste and flavor as an additive.

Preferable amount of troxipide is 50–100 mg t.i.d. and can be adjusted according to the severity of gastritis and/or to the age of patients.

The following examples will further illustrate the present invention without, however, limiting it thereto.

EXAMPLE 1

Aspirin-Induced Gastric Lesions.

Rats weighing about 200 g were fasted for 48 hours and deprived of water for 24 hours. Thereafter, aspirin (Merck) at a dose level of 125 mg/kg was given orally 2 times every 2 hours. The animals were killed 3 hours after the second administration of aspirin. The stomach of each animal was removed and fixed 0.5% neutral formalin solution according to the method of Brodie and Hanson (Gastroenterology 38, 353–360, 1960). The length (mm) of each of the gastric lesions was measured under a dissecting microscope (3 magnifications), summed, and used as an index for evaluation. Troxipide (100, 200 and 300 mg/kg) and cetraxate hydrochloride (100, 300 and 1,000 mg/kg) were orally given an hour before the first administration of aspirin, respectively.

Troxipide (200 and 300 mg/kg) significantly prevented the gastric lesions by 54.4 and 58.7%, respectively. While cetraxate hydrochloride significantly prevented them by 37.7% only at a dose level of 1,000 mg/kg.

EXAMPLE 2

0.6N HCl-Induced Gastric Lesions.

Rats weighing about 200 g were deprived of food and water for 24 hours. One ml of 0.6N HCl solution was given orally and the animals were killed an hour later. Measurement of the gastric lesions was carried out according to the method described in Example 1. Troxipide (100, 200 and 300 mg/kg) and cetraxate hydrochloride (100, 300 and 1,000 mg/kg) were given orally an hour before the administration of 0.6N HCl solution, respectively.

Troxipide (200 and 300 mg/kg) significantly prevented the gastric lesions by 48.6 and 55.6%, respectively. While, cetraxate hydrochloride significantly prevented them by 63.5% only at the dose level of 1,000 mg/kg.

EXAMPLE 3

Water-Immersion Stress-Induced Gastric Lesions.

Rats weighing about 250 g were deprived of food but allowed free access to water for 24 hours. The animals were then immersed vertically to the level of the xiphoid process in a water bath (23° C.) for 7 hours according to the method of Takagi and Okabe (The Japanese Journal of Pharmacology 18, 9–18, 1968) and then killed. Measurement of the gastric lesions was carried out according to the method described in Example 1. Troxipide (100, 200 and 300 mg/kg) and cetraxate hydrochloride (100, 300, 600 and 1,000 mg/kg) were given orally 10 minutes before adding the water-immersion stress.

Troxipide (100, 200 and 300 mg/kg) significantly prevented the gastric lesions by 49.8, 73.7 and 84.9%, respectively. Whereas cetraxate hydrochloride (600 and 1,000 mg/kg) significantly prevented them by 53.2 and 52.0%, respectively.

EXAMPLE 4

Ethanol-Induced Gastric Lesions.

Rats weighing about 200 g were deprived of food and water for 24 hours. One ml of absolute ethanol was given orally and the animals were killed an hour later. Measurement of the gastric lesions was carried out according to the method described in Example 1. Troxipide (100, 200 and 300 mg/kg) and cetraxate hydrochloride (100, 300 and 1,000 mg/kg) were given orally an hour the administration of before ethanol, respectively.

Troxipide (100, 200 and 300 mg/kg) significantly prevented the gastric lesions by 50.7, 60.4 and 79.5%, respectively. Cetraxate hydrochloride (100, 300 and 1,000 mg/kg) also significantly prevented them by 45.3, 67.8, 81.9%, respectively.

Also, the pharmaceutical preparation of the present invention were illustrated by the following examples.

EXAMPLE 5

500 g of troxipide was blended with 375 g of dried cornstarch and 200 g of low-substituted hydroxypropylcellulose. Purified water was then added, and the resultant mixture was kneaded by the usual method of mass granulation. 5 g of magnesium stearate was mixed with the granules to prepare tablets, each tablet having a weight of 108 mg (contained 50 mg of troxipide). The tablets thus prepared were coated with a coating material by the usual spraying method to afford the film coated tablets having a weight of 110 mg for each.

EXAMPLE 6

1,000 g of troxipide was blended with 600 g of dried cornstarch and 350 g of low-substituted hydroxypropylcellulose. Purified water was then added and the resultant mixture was kneaded by the usual method of mass granulation. 10 g of stearic acid was mixed with the granules to prepare tablets, each tablet having a weight of 196 mg (contained 100 mg of troxipide). The tablets thus prepared were coated with a coating material by the usual spraying method to afford the film coated tablets having a weight of 200 mg for each.

EXAMPLE 7

2,400 g of troxipide was blended with 9,120 g of low-substituted hydroxypropylcellulose. This mixed powder was kneaded after adding an aqueous solution dissolving 360 g of hydroxypropylcellulose as binder. The resulting mass was treated to granulate, using 0.5 mm screening, drying and sifting. The granules thus obtained were mixed with 120 g of dried cornstarch to afford fine granules containing 20% troxipide.

What is claimed is:

1. A method of treatment for gastritis comprising administration of an anti-gastritis effective amount of 3,4,5-trimethoxy-N-3-piperidylbenzamide to a patient requiring the treatment.

2. The method of claim 1 wherein the amount of 3,4,5-trimethoxy-N-3-piperidyl benzamide is from about 50 to 100 mg t.i.d.

3. The method of claim 1 wherein the 3,4,5-trimethoxy-N-3-piperidylbenzamide is in the dosage form of tablets, capsules, or granules.

* * * * *